United States Patent [19]

Clark

[11] Patent Number: 4,757,811
[45] Date of Patent: Jul. 19, 1988

[54] INFANT RESTRAINING DEVICE

[76] Inventor: Gerald W. Clark, No. 5, Piney Woods Trailer Ct., Opelika, Ala. 36801

[21] Appl. No.: 928,018

[22] Filed: Nov. 7, 1986

[51] Int. Cl.$^4$ .......................... A61F 5/37; A61G 1/00; A47D 13/02
[52] U.S. Cl. .................................... 128/134; 5/82 R; 5/308; 5/434; 269/328
[58] Field of Search ............... 128/70, 71, 84 R, 84 C, 128/134, 28; D24/3, 99; 269/322, 328; 5/2 R, 3, 101, 82 R, 93 R, 93 B, 58, 308, 431, 434, 436, 440; D6/596

[56] References Cited

U.S. PATENT DOCUMENTS

| | | | |
|---|---|---|---|
| D. 275,322 | 8/1984 | Nakao et al. | D24/3 X |
| 2,700,381 | 1/1955 | Powell | 269/328 |
| 2,700,779 | 2/1955 | Tolkowsky | 5/434 X |
| 2,876,459 | 3/1959 | Ackerson | 4/185 |
| 2,926,054 | 2/1960 | Rodin | 269/328 |
| 3,729,752 | 5/1973 | Huggins | 128/134 X |
| 4,194,732 | 3/1980 | Liebman | 269/328 X |
| 4,300,249 | 11/1981 | Taylor | 128/70 X |

Primary Examiner—Richard T. Stouffer
Attorney, Agent, or Firm—George J. Porter

[57] ABSTRACT

The invention is a self contained infant restraining device (10) used for performing cardiopulmonary resuscitation or other emergency treatment on a patient up to 2 years old. The device (10) has 2 sections (12 and 14) which are normally attached together by use of latches (16). Top section (12) is used to carry and restrain the infant's body. Bottom section (14) contains 2 drawers (52) which are used to carry drugs, medical supplies and instruments for treatment of the infant patient. The top section (12) may be quickly released from bottom section (14) if the user wants to make top section (12) lighter and more portable. The infant's body is placed in indentation (36) of the top surface (28) and securely restrained by a plurality of straps (44) using hook and pile fasteners (46). The infant's head is restrained in head indentation (26) which is equipped with two small sand bag pillows (32) attached to indentation (26) by hook and pile fasterners (33) and (34). Provisions are also made for attachment of a Bashaw Cervical Immobilizer (30) in indentation (26) for stabilizing of the infant's body.

6 Claims, 4 Drawing Sheets

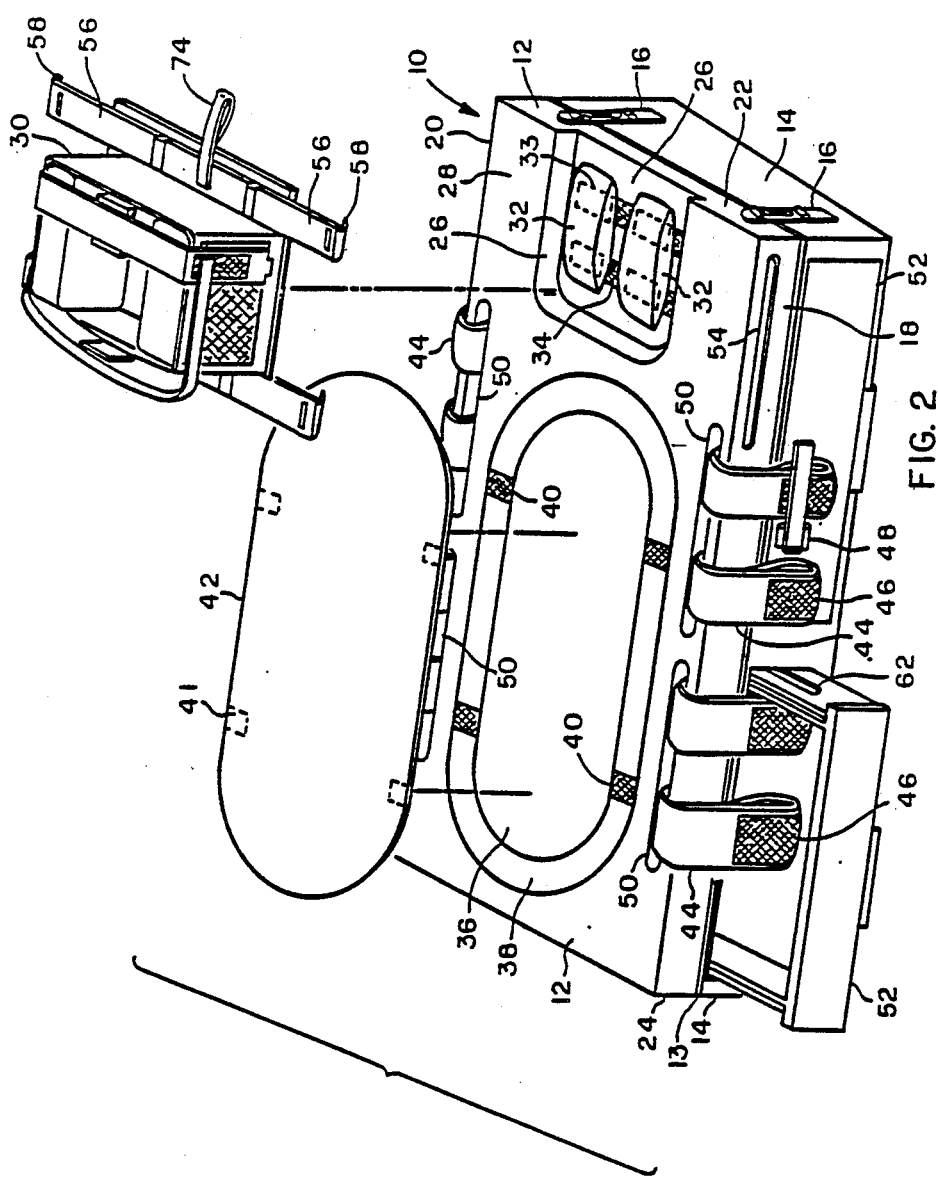

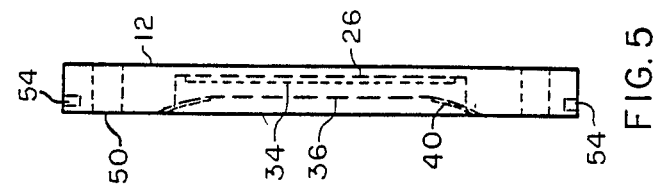
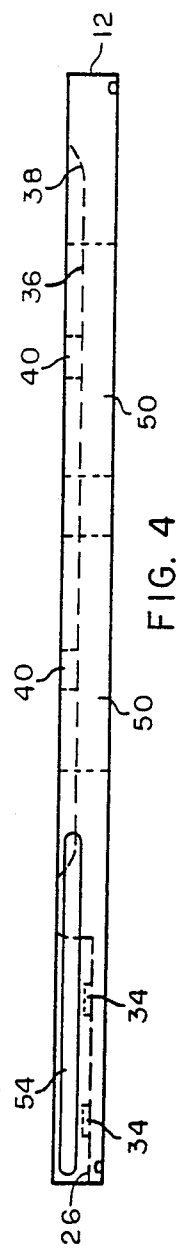
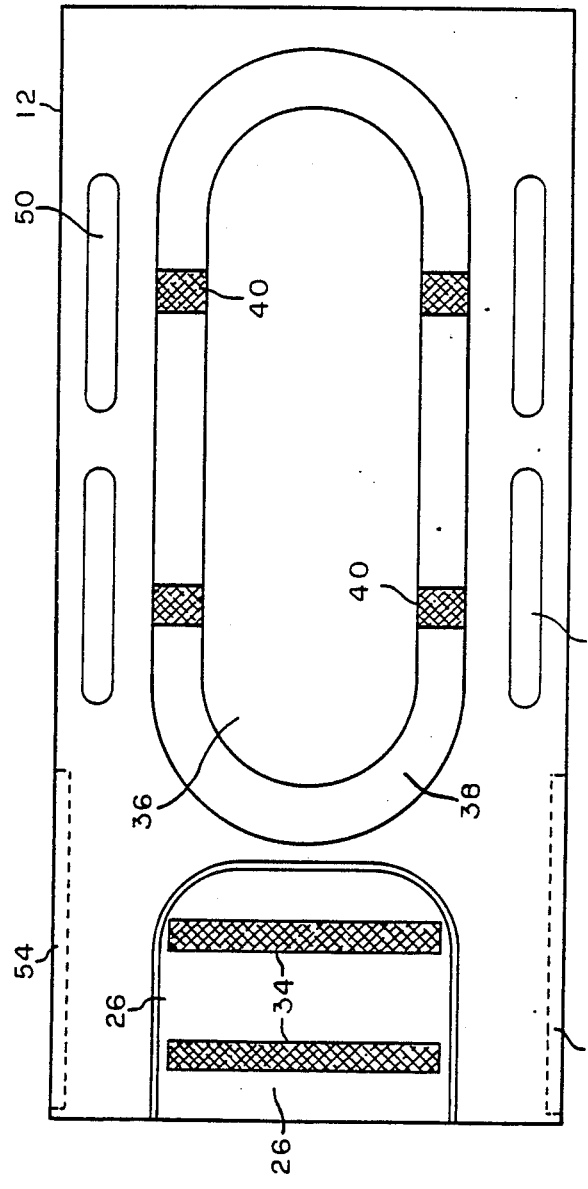

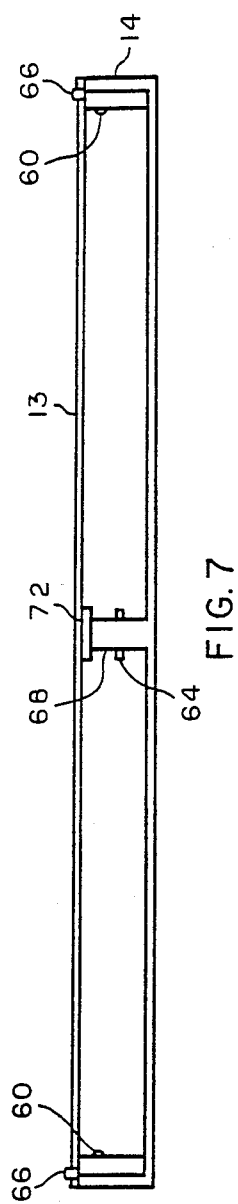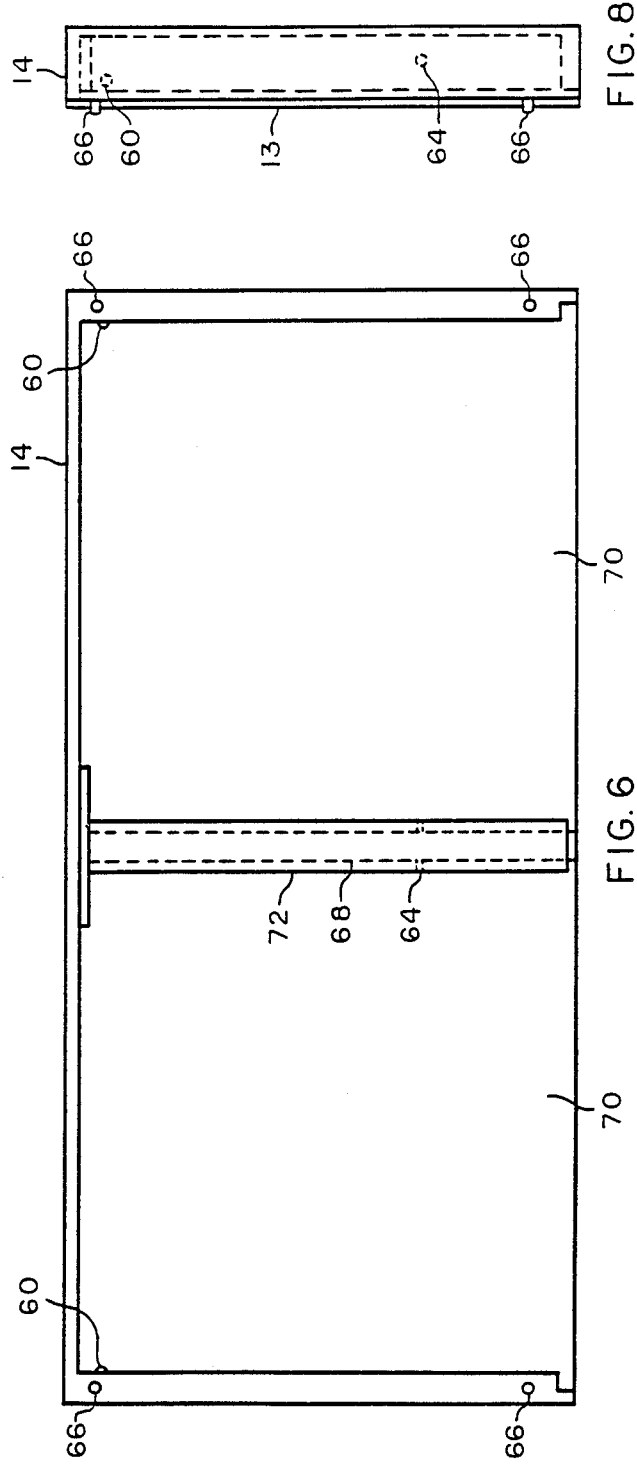

INFANT RESTRAINING DEVICE

TECHNICAL FIELD

The present invention relates to equipment designed for cardiopulmonary treatment of patients and more particularly relates to a board designed to accommodate and support an infant up to age two who requires emergency cardiopulmonary treatment.

BACKGROUND OF THE INVENTION

The applicant has long been aware, during his experience as a paramedic and as an ambulance crew member, that there has been a need for equipment which would make it possible to provide better treatment for infants who are in cardiopulmonary distress or have experienced trauma. More specifically, there has been a need for a device which can firmly support an infant up to two years old, can hold the patient in a very stable condition, can allow the patient's head to be pivoted backward for certain kinds of treatment, is a convenient shape for easy handling, and can be used together with existing types of equipment. Several infant restraining boards are already available, but none of them have all the capabilities mentioned above as being necessary for such cardiopulmonary treatment of infant patients.

U.S. Pat. No. 3,650,523 to DARBY, JR., discloses an infant restraining board which appears to provide secure restraint for an infant. It uses restraining boards to hold the infant's torso, legs, and arms and has an adjustable head restraint. However, this device does not provide for tilting the patient's head backward. Moreover, it is an inconvenient shape, with arm supports sticking out at 90 degrees to the patient's body, and protruding leg supports, each of which sticks out from the patient's body at an acute angle of about 20 degrees with the patient's body. These appurtenances would make it quite difficult for medical personnel to carry a baby in the device while walking and simultaneously perform cardiopulmonary resuscitation.

U.S. Pat. No. 3,306,287 to ARP discloses an infant supporting apparatus having different structure than the present invention and designed for a different purpose, namely, to support an infant during therapeusis, such as respiratory augmentation. This device is a perfectly flat panel which uses a number of upstanding barriers to support and confine the body and head of an infant. One embodiment of the invention has a head cup which holds the head of an infant up in an elevated position. However, the structure of this invention does not provide for and does not contemplate the possibility of lowering the head of an infant or tilting the infant's head backward in order to treat the infant when cardiopulmonary problems are indicated. Moreover, this device is not portable, but instead is intended for stationary use in a hospital or other medical treatment facility.

Still another infant restraining device is shown in U.S. Pat. No. 2,751,268 (U.S. Pat. No. Re. 24,377) to CREELMAN. This device is a flat surgical operating table having a full body cavity in the top surface of the table for holding and supporting an infant in the dorsal recumbent position. Four large pivoting metal arms, with a clamp mounted on the end of each arm, hold the infant on the table. This device appears useful for minor surgical operations not requiring anesthesia, such as circumcisions, but its design does not make it appear to be useful for emergency life support treatment, such as cardiopulmonary distress or trauma. Although this device is described in the patent as being portable, several appurtenances in the form of the four restraint arms and clamps described above would make it difficult to carry easily. It would be particularly difficult for a paramedic to carry the device on his hip and continue cardiopulmonary resuscitation to an infant while walking.

Other infant restraint devices, both of which are quite different from the present device, are shown in the U.S. Pat. Nos. 3,892,399 to CABANSAG and 4,515,155 to WAGEMANN. The device shown in the former patent is an infant seat for immobilizing infants during the taking of X-rays. The latter patent shows a restraint vest for holding a very small infant and keeping the child warm while various medical procedures are performed on the child.

Several devices designed primarily for spinal restraint of accident victims are shown in U.S. Pat. Nos. 4,024,861 to VINCENT, 4,034,748 to WINNER, and 4,519,106 to SANDQUIST. These patents all show devices for supporting only the head and upper torso of adult victims. The patent to VINCENT shows a spine support device in the form of an inflatable bag somewhat similar to an air mattress. The device contains several longitudinal reinforcing ribs. The two latter patents to WINNER and SANDQUIST show substantially flat boards with restraining straps. The patent to WINNER also shows a device having a head restraint with inflatable upstanding sides positioned on either side of a pad which serves as a pillow. However, these devices are not designed for use in cardiopulmonary treatment and do not have the features mentioned above which make it possible to treat that condition.

In view of the foregoing discussion, it will be apparent that the prior art devices do not provide the advantages found in the present invention.

It is therefore an object of the present invention to provide an infant restraining device which is designed particularly for the proper treatment of cardiopulmonary distress and trauma.

It is another object of the present invention to provide an infant restraining device which is lightweight, portable, and of a convenient shape for easy handling.

It is still another object of the present invention to provide an infant restraining device which does not have fixed projections or appurtenances attached to it.

It is yet another object of this invention to provide an infant restraining device which is easy for a paramedic to carry under his arm with the side of the device resting on his hip, while he continues cardiopulmonary resuscitation (CPR) while walking.

It is still another object of the present invention to provide an infant restraining device which is designed to hold an infant firmly and securely in position on the device while the patient's head may be tilted backward or flexed in order to provide intubation to the patient.

It is yet another object of the invention to provide an infant restraining device which is designed for quick and easy installation of a commercially available Bashaw Cervical Immobilizer for use on a trauma case to stabilize the infant's head or alternatively, to quickly and easily install custom-made head stabilizing equipment.

SUMMARY OF THE INVENTION

The present invention is a self-contained infant restraining unit for holding infants who are in cardiopulmonary distress or trauma while cardiopulmonary resuscitation or other emergency life-saving medical procedures are being undertaken. The unit is generally rectangular with two sides, a head end, a foot end, a top surface, a bottom surface, and has two indentations (or hollowed-out areas) in its top surface. The first indentation in the top surface is positioned at the head end of the unit and opens into the head end of the unit. The second indentation in the top surface is elongated and closed and is positioned off-center toward the foot end of the unit. The unit further comprises means for head restraint of the patient and means for restraining the torso and legs of the patient.

BRIEF DESCRIPTION OF THE DRAWINGS

FIG. 2 is an exploded perspective view of the invention showing the top section and the bottom section attached together and the insert for the top section and a Bashaw Cervical Immobilizer both shown exploded from the top section.

FIG. 3 is a plan view of the top section of the infant cardiopulmonary device.

FIG. 4 is a side view of the device as shown in FIG. 3.

FIG. 5 is an end view of the top section of the device as shown in FIG. 3.

FIG. 6 is a plan view of the bottom section of the infant cardiopulmonary device.

FIG. 7 is a side view of the bottom section of the device as shown in FIG. 6.

FIG. 8 is an end view of the bottom section of the device as shown in FIG. 6.

DETAILED DESCRIPTION OF THE INVENTION

Figure 1:
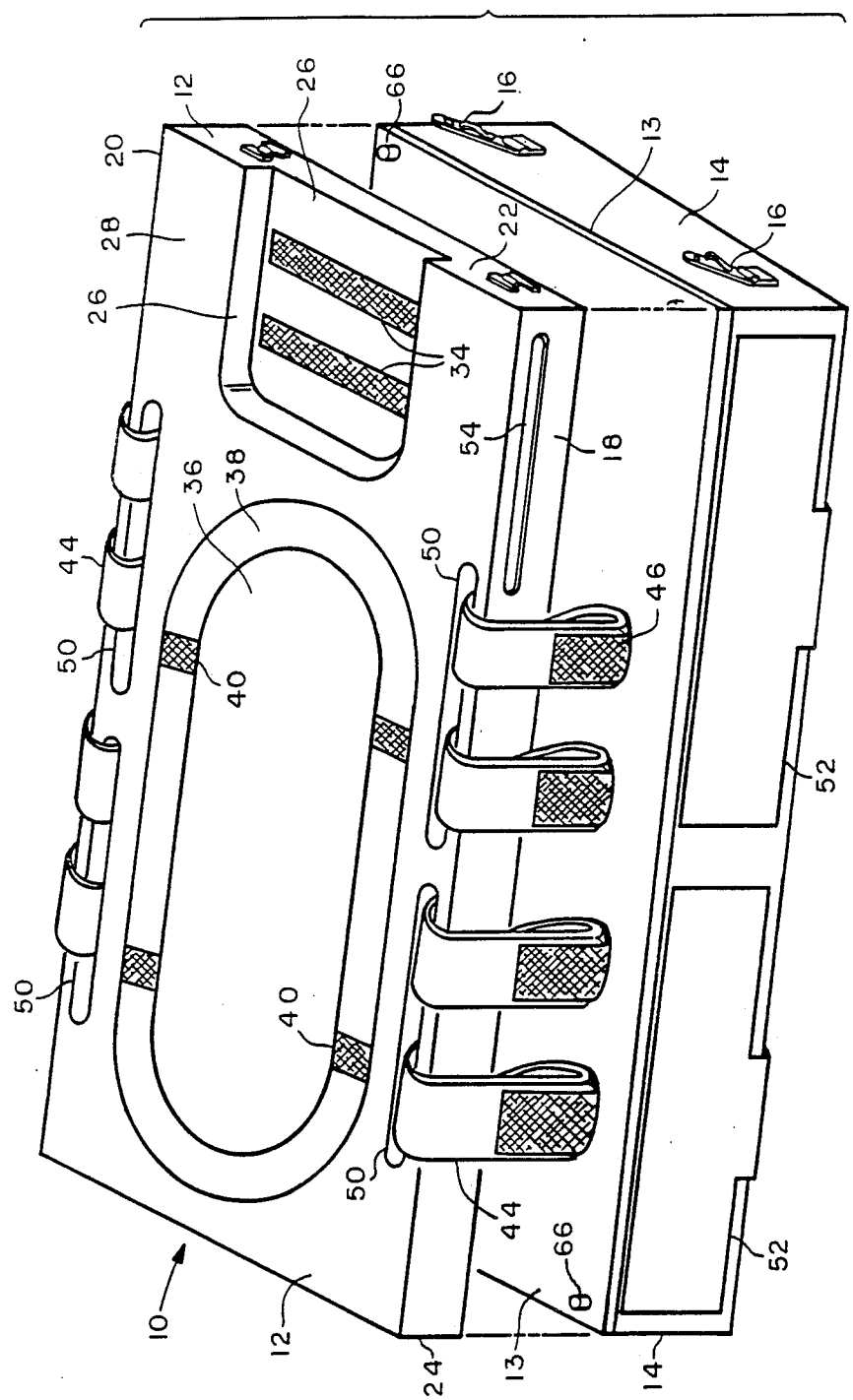
FIG. 1 is an exploded perspective view of the invention showing the top section and the bottom section separated.

The invention is a self-contained infant restraining device used for performing cardiopulmonary resuscitation on a patient up to 2 years old. The device, as shown in FIG. 1, is designated generally by numeral 10. FIG. 1 shows the rectangular board (or top section) 12 and bottom section 14 separated but capable of being attached together by a pair of latches 16 positioned at opposite ends of the infant restraining device 10. Top section 12 of the device 10 has a right side 18, a left side 20, a head end 22, and a foot end 24.

At one end of the device 10 is a generally rectangular cut-out or indentation 26 in the top surface 28 of the device 10. The head indentation 26 allows the head of an infant patient to be tilted backward below the level of the body into a slightly flexed position for intubation. The head indentation 26 also permits the installation of a commercially available Bashaw Cervical Immobilizer 30 (see FIG. 2) for use on a trauma case. When the Bashaw Cervical Immobilizer 30 is not used, small sand bags 32 (see FIG. 2) having hook and pile fasteners 33 can be affixed to hook and pile type fasteners 34 in the head indentation 26 to stabilize the infant's head.

A large oval-shaped indentation 36 in the top surface 28 of top section 12 is provided to enhance patient stability. Beveled sides 38 are provided around the edges of indentation 36 for the safety and comfort of the infant patient. Hook and pile fasteners 40 are attached to the beveled sides 38 of oval-shaped indentation 36 to secure an oval-shaped insert 42 (see FIG. 2) used to fill indentation 36 when desired. A plurality of safety belts 44 having hook and pile type fasteners 46 are attached to top surface 28 by means of slots 50. One or more limb immobilizers 48 may be attached to belts 44 to hold the infant's arms or legs in position.

The exploded perspective view of FIG. 2 shows the device 10 comprising the top section 12, the oval-shaped insert 42, which fits into oval-shaped indentation 36, and the bottom section 14 with two drawers 52. Insert 42 may be positioned and attached into indentation 36 with the aid of hook and pile fasteners 40 on the beveled sides 38 of indentation 36 and hook and pile fasteners 41 on the underside of insert 42. The infant restraining board 10 is generally used without insert 42 when the board 10 is being used for cardiopulmonary resuscitation. In this mode, the patient's torso and legs are stabilized and yet head indentation 26, which is at a lower level than indentation 36 for the body, allows room for the patient's head to be tilted backward for intubation (insertion of an oxygen supply tube). If needed, two small sand bags 32 having attached hook and pile fasteners 33 may be positioned and attached to hook and pile fasteners 34 located in head indentation 26 to stabilize an infant patient's head.

The perspective view of FIG. 2 also illustrates how an alternative arrangement of the invention may be used when cardiopulmonary treatment is not being undertaken. In such a case, insert 42 is positioned and used in indentation 36. Thus, it is possible to use the present invention with a flush surface in the middle and at the foot end 24 of top surface 28 of the device 10, for example, when stabilization of an infant's spine is necessary. FIG. 2 also shows a Bashaw Cervical Immobilizer 30 installed in the head indentation 26 over the top of sand bags 32. The Bashaw Immobilizer 30 is equipped with two elastic straps 56, each strap 56 having two attached hooks 58. With the use of the strap 56 and attached hooks 58, the "Bashaw" 30 attaches to the infant restraining device 10. Two hooks 58 fit into each one of a pair of grooves 54, which are located in the top section 12 of the device, one groove 54 being located on either side of top section 12. When the Bashaw Immobilizer is not being used, it may be secured on a storage hook (not shown) by use of its hanging strap loop 74. This commercially available device, which is used to immobilize an infant's head, is manufactured by Bashaw Medical, Inc., of Pensacola, Fla. 32506.

Two drawers 52 are mounted in one side of bottom section 14. The two drawers in the device 10 are designed to house all the drugs, supplies, and instruments necessary to support treatment of an infant during an emergency. As may be seen best in FIG. 7, drawers 52 are equipped with a drawer lock pin 60 which holds the drawers 52 in the closed position when the drawers 52 are not in use. Looking back at FIG. 2, each drawer 52 has a long horizontal groove 62 cut into one of its sides. This drawer guide and stop groove 62 is for the purpose of guiding the drawer when it is moved in or out. Groove 62 also accommodates drawer guide and stop pin 64 (FIG. 7) and prevents drawers 52 from being pulled all the way out and thereby spilling their contents.

FIG. 3 is a plan view showing the details of top section 12. FIG. 4, which is a side view of the top section 12, illustrates how head indentation 26 is cut somewhat deeper than oval-shaped indentation 36 in order to allow an infant's head to be tilted well-back for intubation of an oxygen supply tube. FIG. 5, which is a side view of top section 12, also illustrates the difference between the depths of head indentation 26 and oval-shaped body indentation 36.

FIG. 6 is a plan view of bottom section 14 of the infant restraining device 10. It should be noted that bottom section 14 is open on top and on one side to accommodate the drawers 52, since the bottom 13 of top section 12 is in effect the top of bottom section 14 when the top section 12 and the bottom section 14 are attached. As may be seen best in FIGS. 6-8, the top of bottom section 14 is equipped with a plurality of upper section guide dowels 66 extending upward from the top of bottom section 14 to guide top section 12 and bottom section 14 together during assembly and to hold them together in the proper position when assembled. Bottom section 14 also has a vertical center wall 68, which divides the bottom section into two compartments 70. A horizontal drawer holder member 72 is attached to the top of center wall 68 to help hold drawers 52 in position. FIGS. 7 and 8 are a side view and end view, respectively, of the bottom section 14 of the infant restraining device 10, as shown in FIG. 6.

In operation, an infant in cardiopulmonary distress or trauma from other causes may be attached to the device 10 while cardiopulmonary resuscitation or other emergency life-saving medical procedures are being undertaken. The infant's torso is placed in oval-shaped indentation 36 and the child is securely fastened to the device 10 by use of a plurality of straps 44 having attached hook and pile fasteners 46. The infant's head is placed upon two small sand bags which are attached by use of hook and pile fasteners 33 and 34 in head indentation 26. Alternatively, the infant's head may be restrained and stabilized by use of a Bashaw Cervical Immobilizer 30 which is installed by use of straps 56 and hooks 58 over the top of sand bags 32 in head indentation 26. In case of spinal injury, the infant is not placed in indentation 36 but, instead, insert 42 is installed in indentation 36 so that the top of insert 42 is flush with the top surface 28 of top section 12. Two drawers 52 are used to conveniently carry all drugs, medical supplies and instruments needed to treat the infant patient.

From the above, it may be seen that the applicant has provided an infant restraining device which facilitates the prompt and efficient treatment of cardiopulmonary distress in infants up to age 2. The device is self-contained in that it provides drawers to house all drugs, supplies and instruments necessary to support treatment during an emergency. The device provides structure which makes it possible to securely hold the infant's body in position and, at the same time, allows the infant patient's head to be tilted or flexed backward for intubation of oxygen equipment. The device may be used with either small sand bags or a Bashaw Cervical Immobilizer for stabilizing the infant's head. The device is lightweight and portable and is designed in a convenient shape without stiff projections or appurtenances so that an infant can be carried with the side of the device resting on the hip of the medic. This makes it possible to continue cardiopulmonary resuscitation while the patient is being carried. The entire unit when fully equipped is still small enough to easily carry to the scene of an accident with other emergency equipment, and it can be stored in any compartment of an ambulance or rescue vehicle.

It will be understood that the invention may be embodied in other specific forms without departing from the spirit or central characteristics thereof. The present examples and embodiments, therefore, are to be considered in all respects as illustrative and not restrictive, and the invention is not to be limited to the details given herein but may be modified within the scope of the appended claims.

I claim:

1. An infant restaining device comprising:
    a rectangular board comprising a top surface, a bottom surface, two sides, a head end and a foot end, said top surface having first and second indentations for accommodating the head and body of an infant, and a plurality of slots in said top surface located near said two sides;
    strap means attached to said rectangular board and running out said slots for holding the body of an infant to said restaining device; and
    a rectangular bottom section comprising:
        four sides, one of said sides having two cavities opening out of it;
        a bottom panel attached to said sides; and
        two drawers, each said drawer being mounted in one of said two cavities;
    said rectangular bottom section being attached to said rectangular board for carrying drugs, supplies and instruments needed to treat an infant patient.

2. The infant restraining device of claim 1 wherein said bottom section comprises latch means to hold each of said drawers in closed position.

3. The infant restraining device of claim 1 wherein each of said drawers is configured with a horizontal groove along one of its sides and said bottom section comprises a stop pin for preventing each of said drawers from being pulled completely out of its said cavity and thereby preventing spillage of the contents of said drawers.

4. An infant restraining device comprising:
    a rectangular board comprising a top surface, a bottom surface, two sides, a head end and a foot end, said top surface having first and second indentations for accommodating the head and body of an infant, and a plurality of slots in said top surface located near said two sides;
    strap means attached to said rectangular board and running out said slots for holding the body of an infant to said restraining device;
    a rectangular bottom section comprising four sides and a bottom panel attached to said sides, said rectangular bottom section being attached to said rectangular board for carrying drugs, supplies and instruments needed to treat an infant patient;
    mating latch means mounted on both said rectangular board and said bottom section for latching said rectangular board and said bottom section together; and
    vertical guide dowels mounted on said bottom section and mating with holes in said bottom surface of said rectangular board for guiding said rectangular board and said bottom section together during assembly and holding said rectangular board and said bottom section together in the proper position when assembled.

5. An infant restraining device comprising:
    a rectangular board comprising a top surface, a bottom surface, two sides, a head end and a foot end, said top surface having a rectangular first indentation opening out of said head end of said rectangular board, for accommodating the head of an infant, a second oval-shaped indentation for accommodating the torso and limbs of an infant, and a plurality of slots in said top surface located near said two sides; and strap means attached to said rectangular board and running out said slots for holding the body of an infant to said restraining device.

6. The infant restraining device of claim 5 wherein said oval-shaped indentation has beveled sides for the comfort and safety of an infant patient being restrained in said device.

* * * * *